United States Patent [19]

Harding et al.

[11] Patent Number: 4,887,285
[45] Date of Patent: Dec. 12, 1989

[54] METHOD AND DEVICE FOR DETERMINING THE SPATIAL DISTRIBUTION OF CHEMICALS IN AN OBJECT

[75] Inventors: Geoffrey Harding, Halstenbek; Josef-Maria Kosanetzky, Norderstedt, both of Fed. Rep. of Germany

[73] Assignee: U.S. Philips Corporation, New York, N.Y.

[21] Appl. No.: 24,656

[22] Filed: Mar. 11, 1987

[30] Foreign Application Priority Data

Mar. 18, 1986 [DE] Fed. Rep. of Germany ....... 3608965

[51] Int. Cl.$^4$ ........................ A61B 6/02; G01N 23/08
[52] U.S. Cl. .......................................... 378/88; 378/86
[58] Field of Search ..................................... 378/88–86, 378/6, 7, 5, 62

[56] References Cited

U.S. PATENT DOCUMENTS

| | | | |
|---|---|---|---|
| 3,843,881 | 10/1974 | Barton, Jr. et al. | 378/88 |
| 4,149,081 | 4/1979 | Seppi | 378/18 |
| 4,314,155 | 2/1982 | Sowerby | 378/88 |

FOREIGN PATENT DOCUMENTS

| | | | |
|---|---|---|---|
| 3406905 | 9/1985 | Fed. Rep. of Germany. | |
| 0019519 | 6/1971 | Japan | 378/88 |
| 2056056 | 3/1981 | United Kingdom | 378/88 |

Primary Examiner—Carolyn E. Fields
Assistant Examiner—Joseph A. Hynds
Attorney, Agent, or Firm—Jack E. Haken

[57] ABSTRACT

The invention relates to a method of determining the share of different chemical elements in a layer of an examination zone. The Compton scattered radiation and the Rayleigh scattered radiation are separately determined and the variation of the differential scatter coefficients derived from the measurement values is influenced by the shares of the various chemical elements contained in the individual pixels. Therefore, the share of these chemical elements can be determined therefrom.

11 Claims, 4 Drawing Sheets

METHOD AND DEVICE FOR DETERMINING THE SPATIAL DISTRIBUTION OF CHEMICALS IN AN OBJECT

The invention relates to a method of determining the spatial structure of a layer of an examination zone which is irradiated by a primary beam along a plurality of beam paths and from a plurality of directions, the radiation emerging from the examination zone at different angles being detected by a detector device in different positions outside the examination zone, after which the differential scatter coefficient is determined for different momentum transfers for each pixel of the layer from the measurement values thus obtained, and also relates to a device for performing the method.

A method of this kind is known essentially from DE-OS 34 06 905. Therein, an examination zone is irradiated by the primary beam at different angles along groups of parallel beam paths. The detector device detects the primary beam emerging from the examination zone as well as the scattered radiation which emerges from the examination zone at a comparatively small scatter angle (up to 12°) with respect to the primary beam. Different scatter angles are covered by different detector elements of the detector device. Subsequently, for each pixel there is formed a pixel value which corresponds to the product of the scatter density (i.e. the number of atoms per unit of volume) in this pixel and the differential scatter cross-section. This product, being referred to hereinafter as the differential scatter coefficient, is a measure (related to the longitudinal dimension of a pixel and the unit of the space angle) of the share of the X-ray or gamma quanta contained in the primary beam scattered in the pixel in the direction determined by a scatter angle.

The following relation exists between the scatter angle $\beta$ and the momentum transfer X:

$$X = 2h \cdot \sin(\beta/2)L \quad (1)$$

Therein, h is Planck's action quantum ($6.63 \times 10^{-34}$ Js) and L is the wavelength of the X-ray or gamma quanta. Therefore, when the energy of the quanta in the rimary beam is known, a momentum transfer X can be unambiguously assigned to each scatter angle. According to the known method, for each pixel of the layer the differential scatter coefficient is thus determined for different momentum transfers.

Because of the small scatter angle, the known method actually covers only the so-called Rayleigh scattered radiation. As is known, Rayleigh scattering is a process during which the gamma quanta are scattered by atomically bound electrons without changing their energy. For the small values of the scatter angle or the momentum transfer used in the known method, the variation of the differential scatter coefficient or the differential scatter cross-section depends essentially on the structure of the molecule containing the atom whose electron causes the Rayleigh scattering.

The present invention, however, has for its object to provide a method which enables quantitative information to be obtained as regards the content of predetermined chemical elements of the layer (or individual pixels in the layer), regardless of their structural assignment.

On the basis of a method of the kind set forth, this object is achieved in that the Compton scattered radiation and the Rayleigh scattered radiation are separately measured at different points, the differential scatter coefficient for Compton scattered radiation and Rayleigh scattered radiation being determined separately from the measurement values for the pixels of the layer, the share of the various chemical elements being determined for individual pixels so that the superposition of the differential scatter cross-sections of these elements, weighted by these shares, as a function of the momentum transfer is at least approximately proportional to the differential scatter coefficients determined for Compton scattering and Rayleigh scattering as a function of the momentum transfer.

The invention is based on the recognition of the fact that, within a given range of the momentum transfer for different chemical elements, the differential scatter cross-section as a function of the momentum transfer varies in a manner which is characteristic of the relevant chemical element for Rayleigh as well as Compton scattered radiation. On the basis of this variation, therefore, it can be determined which chemical element is present in the layer.

A pixel usually contains several chemical elements. When these elements are known, a weighted sum of the (known) differential scatter cross-sections of the individual elements can be formed (by suitable variation of the weighting factors) so that the variation of this sum as a function of the momentum transfer corresponds at least substantially to the measured variation of the differential scatter cross-section as a function of the momentum transfer. The weighting factors of the sum nearest to the measured variation represent the share of the relevant chemical elements in the pixel.

In the method in accordance with the invention, the scattered radiation is preferably determined for momentum transfers in the range $0.5 \leq \times Lo/h \leq 6$, Lo being equal to $10^{-10}$ m ($=1$ Angström). When the energy of the X-ray quanta in the primary beam amounts to, for example approximately 60 keV, this condition will be satisfied for scatter angles in the range of from approximately 6° to 80°.

In the case of smaller scatter angles or momentum transfers, the measurements are influenced by the structure of the molecular compound in which the atoms participating in the scattering process are situated. For reasons of geometry, the upper limit of the scatter angle amounts to approximately 90°.

For the separate measurement of Compton and Rayleigh scattered radiation, use must be made of the fact that the energy of the scattered X-ray quantum is reduced during Comptons scattering, whilst it is sustained during Rayleigh scattering. The detector device, therefore, must have an energy resolving power. However, this power is limited to approximately 300 eV (at 60 keV), for example, in the case of germanium detectors. However, when the quantum energy in the primary beam amounts to, for example 57 keV, only the quanta which emerge at a scatter angle of 18° (or more) will suffer an energy loss of 300 eV or more during Compton scattering. In the case of smaller scatter angles, such detectors cannot separately measure the Compton scattered radiation and the Rayleigh scattered radiation.

Therefore, in a further version in accordance with the invention a first measurement is performed for the scattered radiation in each direction and for each beam path, during which the scattered radiation is incident directly on the detector device, followed by a second measurement during which a filter is inserted between the examination zone and the detector device, the absorption band edge of said filter being situated at a wavelength which is shorter than the wavelength of the Compton scattered radiation produced and which is longer than that of the Rayleigh scattered radiation.

When the wavelength at which the absorption band edge of the filter is situated corresponds to an energy which is only slightly, for example 40 eV, smaller than the quantum energy in the primary beam, the Rayleigh scattered radiation will be more or less suppressed by the filter during the second measurement, so that the Compton and the Rayleigh scattered radiation can be separately determined by comparison of the first and the second measurement.

A device for performing the method, comprising a radiation source for generating gamma rays or X-rays, a diapraghm device for forming a primary beam having a small cross-section for irradiating through an examination zone, a detector device for measuring the primary beam on the other side of the examination zone as well as the scattered radiation produced in the zone irradiated by the primary beam, drive means for realizing translatory and rotary motions between the examination zone on the one side and the radiation source and the detector device on the other side, and an arithmetic device for determining the differential scatter coefficient in the pixels of the layer of the examination zone irradiated by the primary beam, is characterized in that the detector device is constructed so that, upon detection of gamma quanta or X-ray quanta, pulses are generated which have an amplitude which depends on the quantum energy, the pulses being processed in dependence of their amplitude so that the Compton scattered radiation and the Rayleigh scattered radiation can be separately measured, there being provided a storage device in which the scatter cross-sections for Compton scattered raadiation and Rayleigh scattered radiation are stored for different values of the momentum transfer for the chemical elements occurring in the examination zone, the arithmetic device being programmed so that the share of the chemical elements contained in the individual pixels is determined from the measurement values and the values stored in the storage device.

When Compton and Rayleigh scattered radiation is to be separately measured, a radiation source must be used which supplies X-rays or gamma rays which are as monochromatic as possible. This is because in the case of a wideband X-ray or gamma ray spectrum it would not be possible to determine the scattering process (Rayleigh or Compton scattering) from the energy of a scattered quantum, in order to determine of the two scattered radiation shares separately. It is known that isotopes supply exactly monochromatic X-rays, but the intensity thereof is very low. Therefore, the execution of the method in accordance with the invention would require such a long period of time that examinations of living human or animal bodies would hardly be feasible. Therefore, a further version in accordance with the invention is characterized in that the radiation source is formed by an X-ray source having a tantalum anode, and that in its beam path there is arranged a filter for suppressing the short-wave radiation. A further embodiment in accordance with the invention is characterized in that the filter is made of thulium.

It is known that an X-ray source has a retardation radiation spectrum whose maximum energy is determined by the high voltage applied to the X-ray source; for example, when the high voltage amounts to 120 keV, the maximum energy of the X-ray quanta generated amounts to 120 keV. However, in addition to the retardation radiation, the X-ray source also emits characteristic radiation having a line spectrum. Particularly pronounced is the intensity of the so-called $K\alpha_1$-line. It amounts to approximately 10% of the overall intensity. The energy of the $K\alpha_1$-line amounts to 57.524 keV for an X-ray source comprising a tantalum anode. The absorption band edge of the thulium filter is situated at approximately 59.4 keV. Thus, the higher-energetic part of the retardation radiation spectrum is substantially suppressed, whilst the lower-energetic part and notably the $K\alpha_1$-line remain substantially unaffected by the filter.

An X-ray source of this kind in a further version in accordance with the invention comprises an erbium filter which can be inserted between the examination zone and the detector device. Erbium has an absorption band edge which is situated at a wavelength which corresponds to a quantum energy of 57.483 keV. A filter of this kind thus substantially suppresses the Rayleigh scattered radiation evoked by the $K\alpha_1$-line of an X-ray sorce having a tantalum anode, whilst the Compton scattered radiation is hardly influenced thereby. Thus, the use of such a filter enables the separate determination of Compton and Rayleigh scattered radiation by way of two measurements, so that no extremely high requirements need be imposed as regards the energy resolving power of the detector device. Therefore, instead of semiconductor detector elements which usually require cooling and which are expensive, other detector elements, for example scintillation detectors having a sodium iodide crystal can also be used in the detector device.

The invention will be described in detail hereinafter with reference to the drawings. Therein.

Figures 1A, 1B:
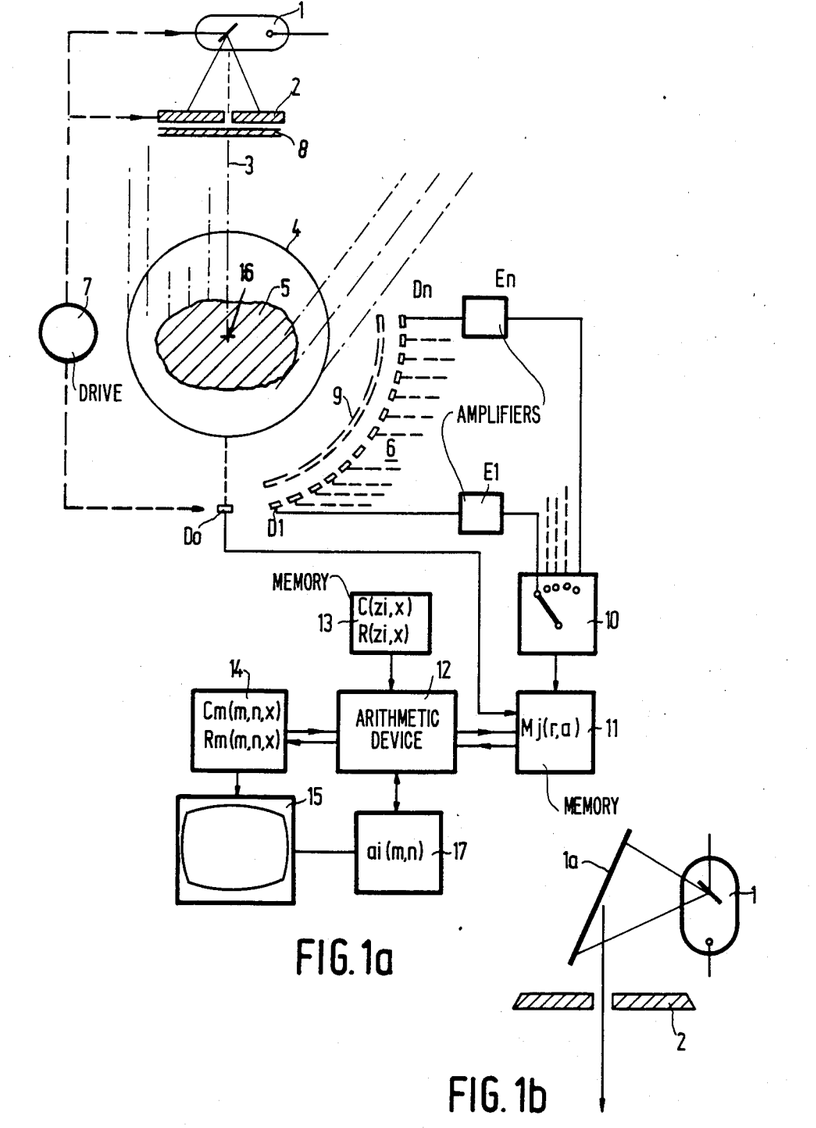
FIG. 1a shows a device for performing the method.
FIG. 1b shows an embodiment of a suitable radiation source.

The reference numeral 1 in FIG. 1a denotes a radiation source in the form of an X-ray source whose radiation beam is stopped so as to form a primary beam 3 having a narrow cross-section (pencil beam) by means of a diapraghm device 2. The primary beam 3 irradiates a circular examination zone 4 which surrounds the object 5, for example a human body to be examined. The radiation emerging from the examination zone is measured by a detector device 6.

There is provided a drive 7 which produces a translatory or rotary relative motion between the examination zone 4 or the body 5 on the one side and the X-ray source 1, the diaphragm device 2 and the detector device 6 on the other side. Thus, the examination zone is first irradiated along a number of beam paths extending parallel to the primary beam 3, and subsequently along mutually parallel beam paths which extend at different angles with respect thereto. The apparatus described thus far with reference to FIG. 1 corresponds to the known first-generation computer tomography apparatus.

Figure 2A:
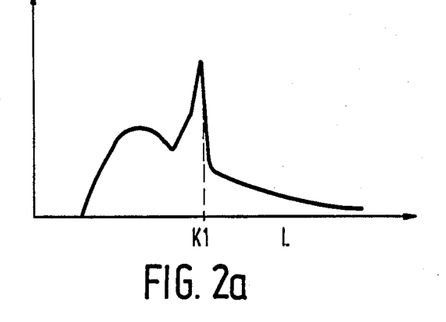
FIGS. 2a to c show the spectrum of the X-ray source used in FIG. 1 in front of and behind the thulium filter, as well as the variation of the attenuation by the erbium filter, FIG. 3 diagrammatically shows a flow-chart of the arithmetic device for determining the shares of the various chemical elements.

The X-ray source 1 comprises an anode which is made of tantalum at least at the area on which the electrons generated by the X-ray source are incident. It operates on a high voltage, for example 100 or 120 kV, which is substantially higher than the characteristic energy of tantalum (57.524 keV). The variation of the spectrum of the X-rays emitted by the anode, therefore, is as shown in FIG. 2a as a function of the wavelength L, the wavelength of the characteristic radiation being denoted by k1.

Between the X-ray source 1 and the examination zone 4 there is arranged a thulium filter 8 whose absorption band edge is situated at approximately 59.335 keV. This filter substantially suppresses the part of the spectrum whose wavelength L is smaller than the value corresponding to the energy of 59.5 keV and conducts the other part, having a longer wavelength, substantially without obstruction. Therefore, the spectrum of the primary beam 3 passing through the examination zone 4 has the (idealized) variation represented by a solid line in FIG. 2b.

Figure 2B:
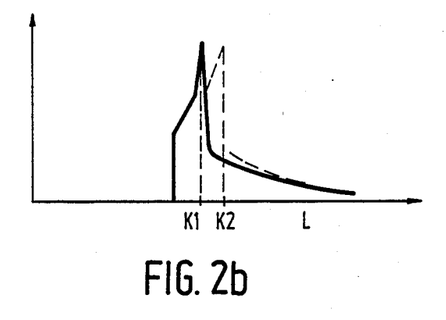

In practice, the retardation radiation cannot be suppressed as well as shown in FIG. 2b. A radiation source in which the retardation radiation spectrum is even further suppressed is shown in FIG. 1b. Therein, use is made of the fluorescent radiation emitted by a tantalum foil 1a when it is exposed to the X-rays of an X-ray source operating at 100–120 kV. The fluorescent radiation has a substantially pure line spectrum whose intensity, however, is smaller than that of the line spectrum of a tantalum X-ray source as shown in FIG. 1a. The thulium filter 8 is still required herein in order to suppress the K$\beta$-line (65 keV).

Purely monochromatic radiation is obtained when use is made of a radionuclide radiation source, preferably americium 241. The energy of this radiation is 59.537 keV. The filter 8 would then be superfluous.

The detector device 6 consists of a number of detector elements D0,D1, . . . Dn. The detector element D0 receives the primary beam 3 at the other side of the examination zone. Therefore, the measurement value supplied thereby is a measure of the attenuation of the primary beam. The detectors D1 . . . Dn are arranged so that they are not struck by the primary beam 3, but only by the scattered radiation produced in the examination zone 4 by the primary beam 3. The number of detector elements and their arrangement is chosen so that for scatter angles of between approximately 6° and 80°, the scattered radiation from essentially every point along the primary beam 3 is intercepted by as many detector elements as there are chemical elements present in the body 5. Therefore, for the examination of a human body at least six detector elements must be present because, ignoring a small residue, the human body consists of oxygen, hydrogen, carbon, nitrogen, phosphor and calcium, said detector elements detecting the scattered radiation generated by a point in the examination zone by the primary beam 3 in an angular range of from 6° to 80°.

Because the X-ray quanta in the primary beam 3 which are scattered by a Compton scattering process loose energy, the spectrum of this type of scattered radiation is shifted towards longer wavelengths as denoted by a broken line in FIG. 2b. The wavelength of the K$\alpha$-line is then shifted from k1 to k2. The extent of the shift depends on the scatter angle. For a scatter angle of a 12°, the wavelength variation corresponds to an energy difference of approximately 140 eV. For a scatter angle of 180°, the shift corresponds to an energy difference of 4900 eV.

Between the examination zone 4 and the detector device 6 there is arranged an erbium filter 9 in such a manner that it can occupy two positions: a first position in which the scattered radiation can reach the detector elements D1 . . . Dn without being obstructed by the filter 9, and a second position in which the radiation can reach the detector elements only through the filter 9.

Figure 2C:
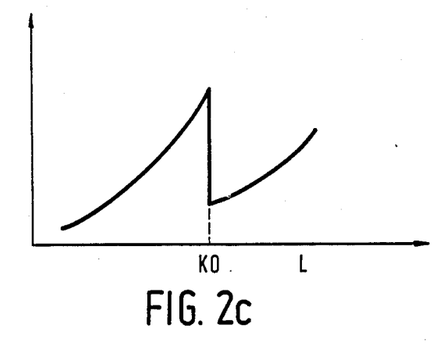

The variation of the attenuation of the erbium filter as a function of the wavelength L is diagrammatically shown in FIG. 2c. It appears that the attenuation of the filter initially increases monotonously as the wavelength increases and abruptly decreases to a lower value at a wavelength ko, after which it increases again. The transient of the attenuation factor at the wavelength ko represents an absorption band edge of the filter 9. The K-absorption band edge has a wavelength which corresponds to a quantum energy of 57,483 keV. Thus, it is situated only 40 keV below the energy of the X-rays (k1) characteristic of tantalum. Thus, the filter 9 has distinctly different attenuation values for the Rayleigh scattered radiation (solid lines in FIG. 2b) and the Compton scattered radiation (broken lines).

Therefore, when two measurements are performed, i.e. one with the filter and one without the filter, the Rayleigh and the Compton scattered radiation share will enter the resultant measurement values with a differengt weight. The share of the Compton scattered radiation and the Rayleigh scattered radiation can be separately determined therefrom when the variation of the attenuation of the erbium filter 9 as a function of the attenuation is known (see FIG. 2c). When use is made of an americium 241 radiation source, the filter 9 should consist of thulium in order to enable suppression of the Rayleigh scattered radiation.

Each of the detector elements D1 . . . Dn is succeeded by a processing unit E1 . . . En, FIG. 1, however, shows only the units E1 and En. In response to the detection of a scattered X-ray quantum, each detector element D1 . . . Dn generates a pulse whose amplitude is proportional to the energy of the X-ray quantum. These pulses are amplified in the units E1 . . . En and are subjected to a pulse amplitude analysis. Only pulses which exceed a given amplitude, and which hence originate from X-ray quanta whose energy is smaller than the value corresponding to the wavelength K1 and larger than the value corresponding to the wavelength k2, are counted in a counter included in each unit. Thus, the counter position is a measure of the intensity of the scattered radiation. This information is applied to a memory 11 via a multiplexer 10. Effects which are not dependent or not directly dependent on the object (multiple scattered radiation, detector sensitivity, alignment of the detector elements with respect to the primary beam, etc.) are preferably eliminated in advance by multiplication of the measurement values by correction factors. The correction factors are derived from calibration measurements performed on objects whose scattering behaviour is known (for example, water). After completion of measurement, the memory will thus contain two measurement values for the Compton and the Rayleigh scattered radiation for each beam path, each direction and each detector, or two measurement values wherefrom the two scattered radiation shares can be derived.

From the values stored for the individual pixels of the examination zone, an arithmetic device 12 determines the respective differential scatter coefficients as a function of the momentum transfer and therefrom the contribution of the chemical elements in the individual pixels.

Figure 3:
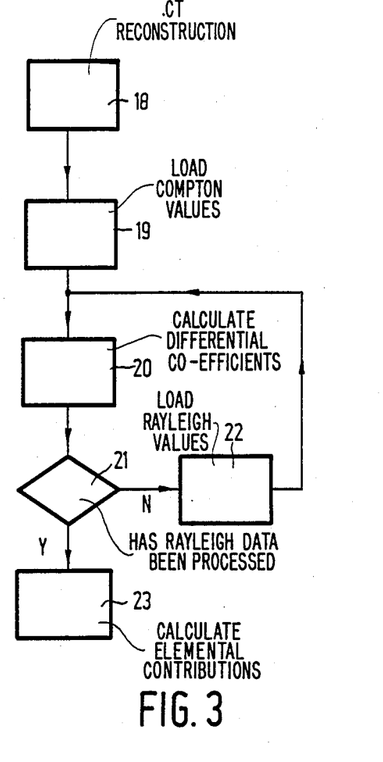

FIG. 3 illustrates the determination of the contribution of the various chemical elements on the basis of a flow-chart. In block 18 the spatial distribution of the attenuation in the layer of the examination zone 4 irradiated by the primary beam 3 is determined from the measurement values formed by the detector element Do. This operation is performed in the manner known from computer tomography. It will be appararent that the output signals of the detector element Do must be amplified and converted into digital data words in a digital-to-analog converter before they can be processed by the arithmetic device 12. For the sake of clarity, the components necessary for performing this operation have been omitted in FIG. 1.

Block 19 relates to the loading of the measurement values for the Compton scattering. In block 20 the differential scatter coefficients for Compton scattering for the pixels of the layer of the examination zone 4 are determined as a function of the momentum transfer.

During branch operation 21 it is checked whether the measurement values for the Rayleigh scattered radiation have already been processed. Because this is not the case initially, the program proceeds to block 22 during which these measurement values are loaded. Subsequently, in block 20 the differential scatter coefficient for Rayleigh scattered radiation is itteratively determined from these measurement values for each pixel of the layer. After the renewed checking, the program proceeds to block 23 inwhich the contribution of the various chemical elements of the matter in the individual pixels is determined from the differential scatter cross-sections for the Rayleigh scattered radiation and the Compton scattered radiation.

Figure 4:
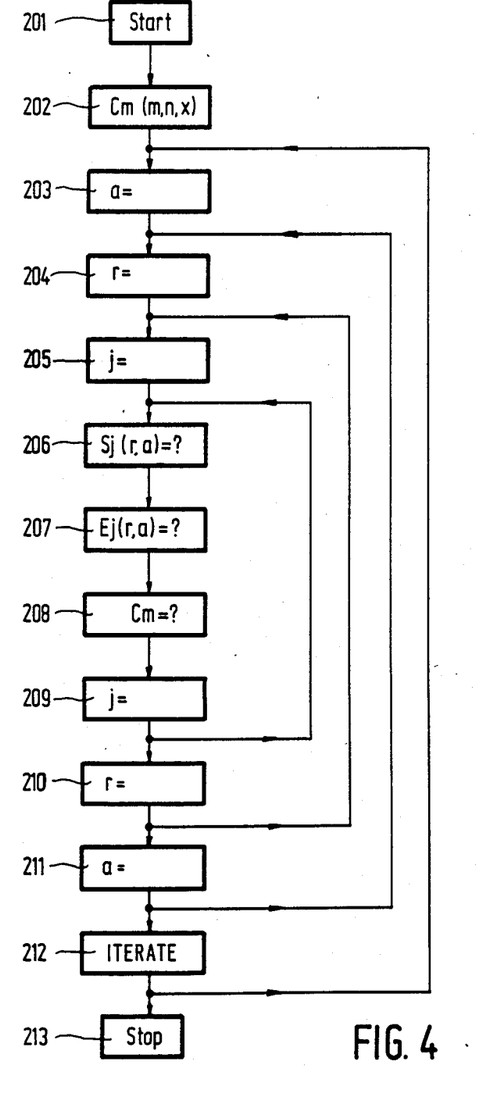
FIG. 4 shows a detail of such a flow-chart.

FIG. 4 shows a flow-chart of the block 20 for determining the differential scatter coefficient Cm for Compton scattered radiation for all pixels of the layer and for different momentum transfers. The differential scatter coefficient Rm for Rayleigh scattered radiation is calculated in the same way.

Figure 5A:
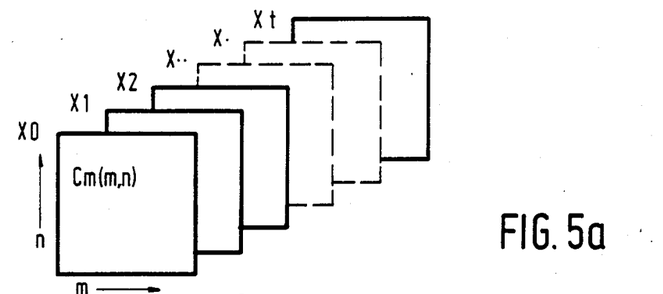
FIGS. 5a to c show different diagrams illustrating the calculations performed during the routine shown in FIG. 4.

After the start (step 201), the differential scatter coefficient Cm is given for all pixels m,n and for different momentum transfers X. In accordance with FIG. 5a, for each momentum transfer Xo, X1, X2, ... Xt there is obtained an image which shows the spatial distribution of the differential scatter coefficients for the relevant momentum transfer. In other words, for each pixel, being defined by the column m and the row n in which it is situated, the differential scatter coefficient Cm is determined as a function of the momentum transfer X. The number of different momentum transfers for which this operation is performed must at least be equal to the number of chemical elements present in the examination zone and not larger than the number of detector elements D1 ... Dn provided for intercepting the scattered radiation.

The presetting of the differential cross-sections is arbitrary. For example, it may be assumed that water is present throughout the examination zone 4, so that for each momentum transfer and for all pixels the same differential scatter coefficient is obtained which exhibits the same variation as a function of the momentum transfer as the differential scatter cross-section of water. This initial distribution need not be preset again for each examination. It may be stored in a memory so that it need only be fetched therefrom.

During the next step 203, the angle a characterizing the direction of the beam path is preset and in step 204 the distance r between the beam path and the centre 16 (see FIG. 5b) is preset. During the next program step 205, a detector element Dj is selected from the detector elements D1 ... Dn.

Figure 5B:
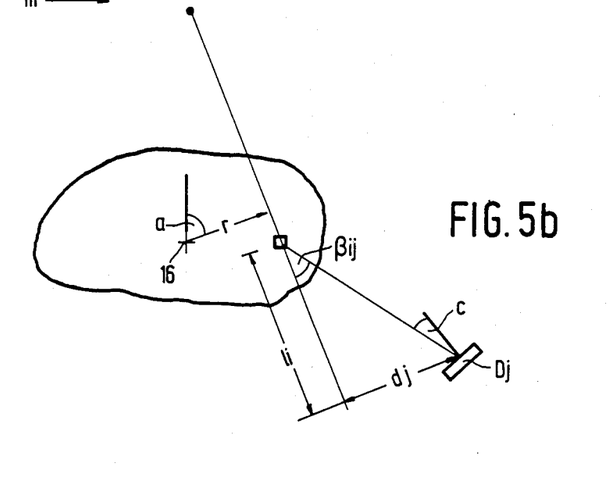

During the program step 206, the scattered radiation is calculated which would be measured by the detector Dj if the primary beam had passed through the examination zone along the beam path defined by the parameters r and a and if the assumed distribution of the differential scatter cross-sections corresponded to the actual distribution. To this end, for the $i^{th}$ pixel on the beam path there is calculated the scatter angle $\beta ij$ with which the scattered radiation produced in this pixel is incident on the detector Dj (see FIG. 5b). The angle $\beta ij$ is calculated in accordance with the equation:

$$\beta ij = \arctan(dj/li) \qquad (2)$$

Therein, dj is the distance between the detector element Dj and the beam path and li is the distance between the base of the normal from the detector to the beam path and the pixel (see FIG. 5b). When the scatter angle $\beta ij$ is known, the momentum transfer can be calculated in accordance with:

$$Xij = 2h \cdot \sin(\beta ij/2)/L \qquad (3)$$

For Rayleigh scattered radiation, the wavelength L then corresponds to the wavelength of the radiation in the primary beam, whilst for Compton scattered radiation this wavelength must be determined from said wavelength and the scatter angle $\beta ij$ in accordance with the known equation for the wavelength variation in the case of Compton scattered radiation. Finally, there is determined the space angle Doij which is covered by the detector Dj measuring the scattered radiation formed in the $i^{th}$ pixel. This angle is calculated as follows:

$$Doij = F \cdot \cos c/(dj^2 + li^2) \qquad (4)$$

Therein, F is the measurement surface area of the detector element Dj and c is the angle enclosed by the normal to the measurement surface with respect to the direction of the scattered radiation.

Figure 5C:
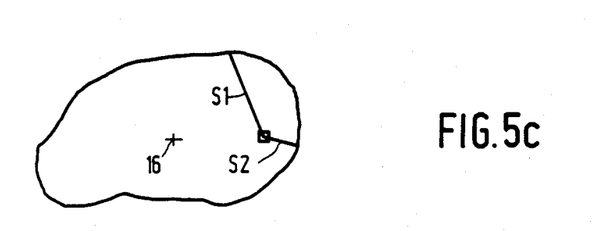

There is also determined the attenuation Tij experienced by the primary beam along its path S1 to the $i^{th}$ pixel (see FIG. 5c) and along its path S2 from this pixel to the detector element Dj. Because the wavelength of the radiation along the paths S1 and S2 is known and because the attenuation along the paths S1 and S2 is known from the previously calculated computer tomogram (block 18), Tij can be accurately determined.

The calculation of the attenuation and the calculations in accordance with the equations (2) to (4) are repeated for all M pixels situated along the beam path characterized by the parameters a and r within the examination zone 4. Subsequently, the intensity of the scattered radiation incident from the beam path onto the detector element Dj is calculated as follows:

$$Sj(r,a) = d \cdot \sum_{i=1}^{M} Cm(i, Xij) \cdot Doij \cdot Tij \qquad (5)$$

-continued $$d = \text{constant}$$

Therein, $Cm(i, X_{ij})$ is the differential scatter cross-section for the momentum transfer $X_{ij}$ and the $i^{th}$ element along the beam path. Because the position of the beam path is defined by $r$ and $a$, with each element $i$ along the beam path there can be associated a pixel with the parameters $m$ and $n$, so that the value $Cm(i, X_{ij})$ can be determined from the given data $Cm(m, n, X)$. Generally, the $i^{th}$ element along the beam path does not occupy exactly the same position in space as a pixel characterized by $m$ and $n$. Similarly, $X_{ij}$ generally is not identical to one of the momentum transfers $X0, X1, X2 \ldots, Xt$. In these cases the value $Cm(i, X_{ij})$ must be determined by interpolation between neighbouring pixels or neighbouring momentum transfers.

The value $Sj(r,a)$ thus determined must be identical to the value $Mj(r,a)$ measured by the detector $Dj$ if the predetermined distribution $Cm(m,n,X)$ corresponds to the actual distribution. Generally, this will not be the case so that a correction value $Ej(r,a)$ can be calculated in accordance with the equation:

$$Ej(r,a) = Sj(r,a) - Mj(r,a) \qquad (6)$$

(step 207). The calculated correction value $Ej(r,a)$ is a measure of the deviation of the actual scatter coefficient for the various pixels and the various momentum transfers from the calculated values and can thus be used for correcting the stored differential scatter coefficient.

During this correction (step 208), all differential scatter coefficients used for calculating of $Sj(r,a)$ in accordance with the equation (5) are corrected, that is to say with a weight which is same as their weight upon entering the equation (5). These values of the differential scatter coefficient are corrected in that a given part $b$ of the correction value $Ej(r,a)$ is added to the value obtained thus far, so that the equation $$Cm: = Cm + b \cdot Ej(r,a) \qquad (7)$$

is obtained. Thus, after the step 208 a part of the values $Cm(m,n,X)$ has been corrected in accordance with the measurement value $Mj(r,a)$ provided by the detector element $Dj$.

Subsequently (step 209), another detector element is selected and the steps 206 to 208 are executed again for this detector element, until for the beam path $r,a$ the measurement values of all detector elements $D1 \ldots Dn$ have been corrected in accordance with the measured scatter intensities $M1(r,a) \ldots Mn(r,a)$.

Subsequently, a new beam path is selected by variation of the value $r$, i.e. the distance between the beam path and the centre 16 of the examination zone 4 (step 210) so that a beam path which neighbours the previous beam path and which extends parallel thereto is established. For this beam path the seps 205 to 209 are repeated, after which the next beam path is adjusted etc. until the correction for all beam paths passing through the examination zone 4 in the direction determined by a has been completed.

Subsequently, a different direction $a$ of the beam paths is adjusted (step 211) and the steps 204 to 211 are repeated until all angular positions in which the primary beam has passed through the examination zone during the measurement have been processed. This first iteration may be followed (step 212) by further iterations, the steps 203 to 211 then being executed several times. The number of iterations may be fixed. However, it is alternatively possible to interrupt the iteration when the corrections in the step 207 constantly remain below a given threshold value. Thus, a corrected distribution $Cm(m,n,x)$ is obtained which very well approximates the actual distribution. From these distributions the share of the various chemical elements in the individual pixels can be determined.

The distributions $Cm(m,n,X)$ are stored in a memory 14 and can be displayed (next to the computer tomogram) on a display monitor 15 (FIG. 1). Thus, as a function of the momentum transfer $X1, X2, \ldots Xt$ for each individual pixel, a series of values $Rm(X)$ is obtained for the Rayleigh scattered radiation and a series of values $Cm(X)$ for the Compton scattered radiation. Because the differential scatter cross-section depends on the chemical elements contained in the pixel in this range of the momentum transfer, the share of these chemical elements in the matter of the pixel can be determined from the variation of the values $Rm(X)$ and $Cm(X)$, respectively.

This can be explained as follows. The differential scatter cross-section for a single atom depends on the one hand on the momentum transfer and on the other hand on the atomic number $Z$ of the relevant atom. The differential cross-section $ds/do$ for Compton scattered radiation, therefore, can be split into a factor $C(Z)$ and a factor $Q(X)$, so that the following equation is obtained:

$$ds/do(Z,X) = C(Z,X) \cdot Q(X) \qquad (8)$$

Therein, $Q(X)$ is the differential cross-section which is calculated in accordance with the known Klein-Nishina formula (see, for example Enzyclopädie Naturwissenschaft und Technik, Zweiburgen-Verlag, Weinheim, page 734, equation (5)) and which depends exclusively on the momentum transfer and not on $Z$ or the type of atom. $C(Z)$ is the so-called scatter function which has already been calculated or measured as a function of the momentum transfer for the various chemical elements. These known values $C(Z)$ are stated, inter alia in the standard tables by Hubbell, Veigele, Briggs, Brown, Cromer and Howerton, J. Phys. Chem. Ref. Data 4, pages 471 to 538, 1975; in this publication $C(X,Z)$ is denoted as $S(q,Z)$.

Because $Q(X)$ is independent of the type of atom or the relevant chemical element, the differential scatter coefficient $Cm(X)$ can be determined in accordance with the following equation:

$$Cm(X) = Q(X) \sum_i N(i) \cdot C(Z_i, X) \qquad (9)$$

Therein, $N(i)$ is the number of atoms of a chemical element in the relevant pixel and $C(Z_i, X)$ is the scatter function for this element. Therefrom, the following is obtained:

$$Cm(x) \sim \sum_i a_i C(Z_i, X); \quad a_i = N(i)/\Sigma N(i) \qquad (10)$$

Therein, $a_i$ is the share of the atoms of a chemical element $i$ in a pixel in relation to the total number of atoms in the pixel, and Zi is the atomic number of the element i.

Similarly:

$$Rm(X) \sim \sum_i a_i R(Z_i,X) \quad (11)$$

Therein, $R(Z_i,X)$ is the scatter function of the chemical element having the atomic number Zi for Rayleigh scattered radiation. The individual values of this function correspond to the square of the atomic form factor which is also stated (as the symbol $F(q,z)$) in the standard tables by Hubbell et al.

Thus, in accordance with the equations (10) and (11) the differential scatter coefficient (for Compton and Rayleigh scattered radiation) is proportional to the sum, weighted by the shares ai, of the scatter functions for Compton and Rayleigh scattered radiation, respectively. The differential scatter coefficients $Cm(X)$ and $Rm(X)$ are known (by measurement and iteration) and the scatter functions $C(Z_i,X)$ and $R(Z_i,X)$ are also known. Thus, it is merely necessary to determine the (unknown) shares ai whereby the values of the scatter function are weighted so that the weighted sums exhibit the same variation as a function of the momentum transfer as the previously determined differential scatter coefficients. This object can in principle be achieved when the differential scatter cross-sections (and the scatter functions) are known for at least as many different values of the momentum transfer as there are different chemical elements present in the examination zone. For the examination of the human body, these elements are essentially only the previously mentioned six chemical elements, so that said values must be known for at least six different momentum transfers.

From literature on mathematics (for example, Journal of the Institute of Mathematics, Vol. 9, pages 91–108, 1972) numerical (so-called fitting) methods are known whereby the shares ai can be determined, using the least squares method, so that, using the equations (10) and (11), the variations of the weighted sums is as proportional as possible to the variation of the differential scatter coefficients. The values ai determined for the various chemical elements are proportional to the share of the relevant chemical element, expressed as an atomic percentage, in the matter of the relevant pixel.

It would in principle be possible to determine the values ai in accordance with the equation (10) or (11) merely by measuring the Compton scattered radiation or the Rayleigh scattered radiation. In that case, however, unavoidable measurement errors cause inaccuracies which can be substantially reduced by measurement of both scattered radiation shares and by solving the equations (10) and (11).

The determination of the shares of the various chemical elements can in principle be performed for all pixels of the layer 4. In that case it is possible to determine the spatial concentration of the chemical elements within the layer. This concentration can then be stored in the memory 17 for display on the display unit 15, when desired.

What is claimed is:

1. A method for determining a spatial distribution of chemicals in an object comprising the steps of:
    scanning a plane layer of the object with a narrow beam of primary radiation from a plurality of directions along a plurality of beam paths;
    separately measuring values of Compton scattered radiation and Rayleigh scattered radiation which is scattered in the object at a plurality of different angles from said beam of primary radiation at points along each of said beam paths;
    from said measured values calculating a differential scatter coefficient for Compton scattered radiation and a differential scatter coefficient for Rayleigh scattered radiation at each of a plurality of pixels in the layer; and then
    at each of said pixels, calculating ratios of relative contributions of radiation scattered from each of a plurality of chemical elements so that a superposition of differential scatter cross-sections for said elements, weighted by said ratios, is at least approximately proportional to the calculated scatter coefficients for Compton scattered radiation and for Rayleigh scattered radiation at each pixel.

2. A method as claimed in claim 1, wherein scattered radiation is measured for momentum transfers X in the range $0.5 \leq XL_o/h \leq 6$, where h is Planck's constant and $L_o = 10^{-10}$ m.

3. The method of claim 1 or 2 wherein the step of measuring the values of scattered radiation comprises measuring all scattered radiation incident on a detector at a particular relative position with respect to a beam path, filtering said scattered radiation incident on said detector using a filter having an absorption band edge which is shorter than the wavelength of said Compton scattered radiation and longer than the wavelength of said Rayleigh scattered radiation, and measuring the wavelength of the filtered radiation.

4. A device for measuring a distribution of chemical elements in an object comprising
    radiation means, including a radiation source, which scan a plane layer of the object with a narrow beam of primary radiation from a plurality of directions along a plurality of beam paths;
    a plurality of detectors distributed adjacent said layer which measure the energy of radiation which is scattered in the object from said beam of primary radiation at a plurality of angles relative to each of said beam paths;
    means which receive signals from said detectors and separately calculate values of Compton scattered radiation and Rayleigh scattered radiation which is scattered at a plurality of different angles from said beam of primary radiation at points along said beam paths;
    computed tomography means which receive said values of Compton scattered radiation and Rayleigh scattered radiation and which calculate a differential scatter coefficient for Compton scattered radiation and a differential scatter coefficient for Rayleigh scattered radiation at each of a plurality of pixels in the layer;
    a memory which stores scatter cross section data values for Compton scattered radiation and Rayleigh scattered radiation at different values of momentum transfer for a plurality of possible chemical elements which may be present in the object; and
    means which use the stored cross section data values to calculate, for each of said pixels, ratios of relative contributions of radiation scattered from each of a plurality of chemical elements so that a superposition of differential scatter cross-sections for said elements, weighted by said ratios, is at least approximately proportional to said calculated scatter coefficients for Compton scattered radiation and for Rayleigh scattered radiation at each pixel.

5. A device as claimed in claim 4, wherein radiation source comprises an X-ray tube having a tantalum anode and, a filter for suppressing the short wave radiation.

6. A device as claimed in claim 3, wherein the radiation source includes an X-ray source, a tantalum foil disposed to produce fluorescent radiation when excited by said X-ray source, and a filter disposed to suppress short wave radiation produced by the foil.

7. A device as claimed in claim 5 or 6, wherein the filter consists of thulium.

8. A device as claimed in claim 4 or 5 further comprising an erbium filter which is selectively insertable between the layer and the detectors.

9. A device as claimed in claim 4, characterized in that for the radiation source use is made of the radionuclide americium 241, and that a filter which is made of thulium is selectively insertable between the examination zone and the detectors.

10. A device as claimed in claim 7, further comprising an erbium filter which is selectively insertable between the layer and the detectors.

11. A device as claimed in claim 4 wherein the radiation source comprises americium 241 and further comprising a thulium filter which is selectively insertable between the layer and the detectors.

* * * * *